(12) United States Patent
Haaland et al.

(10) Patent No.: US 9,695,113 B2
(45) Date of Patent: *Jul. 4, 2017

(54) ALTERNATIVE PROCESS FOR THE PURIFICATION OF AN INTERMEDIATE IN THE SYNTHESIS OF NON-IONIC X-RAY CONTRAST AGENTS

(71) Applicant: GE Healthcare AS, Oslo (NO)

(72) Inventors: Torfinn Haaland, Spangereid (NO); Arne Askildsen, Lindesnes (NO); Rita Heskestad Kalleberg, Lindesnes (NO); Sumihar Silalahi, Lindesnes (NO); Alf Martin Farbrot, Lindesnes (NO); Inger Dagny Saanum, Lindesnes (NO)

(73) Assignee: GE Healthcare AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 15/100,818

(22) PCT Filed: Dec. 8, 2014

(86) PCT No.: PCT/EP2014/076873
§ 371 (c)(1),
(2) Date: Jun. 1, 2016

(87) PCT Pub. No.: WO2015/082718
PCT Pub. Date: Jun. 11, 2015

(65) Prior Publication Data
US 2016/0289174 A1 Oct. 6, 2016

Related U.S. Application Data

(60) Provisional application No. 61/912,807, filed on Dec. 6, 2013, provisional application No. 61/969,959, filed on Mar. 25, 2014.

(51) Int. Cl.
C07C 231/24 (2006.01)
C07C 231/02 (2006.01)
C07C 237/46 (2006.01)

(52) U.S. Cl.
CPC ........... *C07C 231/24* (2013.01); *C07C 231/02* (2013.01)

(58) Field of Classification Search
CPC ........................... C07C 231/24; C07C 231/02
See application file for complete search history.

(56) References Cited

U.S. PATENT DOCUMENTS 4,250,113 A * 2/1981 Nordal ............... C07C 237/46
424/9.454
6,610,885 B1 * 8/2003 Gulbrandsen ......... C07C 231/08
564/153
(Continued)

FOREIGN PATENT DOCUMENTS

CN 1132743 * 10/1996
EP 2277851 * 1/2011
(Continued)

OTHER PUBLICATIONS

International Search Report and Written Opinion regarding International Application No. PCT/EP2014/076873, mail date Feb. 13, 2015, 11 pages.

*Primary Examiner* — Jafar Parsa
*Assistant Examiner* — Amy C Bonaparte
(74) *Attorney, Agent, or Firm* — Wood IP LLC

(57) ABSTRACT

Alternative continuous downstream processes for the production of 5-acetamido-N,N'-bis(2,3-dihydroxypropyl)-2,4,6-triiodoisophthalamide ("Compound A") are described. Compound A is a key intermediate in the production of iodixanol and iohexol, which are two of the biggest commercially available non-ionic x-ray contrast media agents.

9 Claims, 2 Drawing Sheets

(56) References Cited

U.S. PATENT DOCUMENTS

2003/0236407 A1* 12/2003 Schafer .............. A61K 49/0438
 544/384
2011/0021828 A1* 1/2011 Homestad ............ B01D 61/027
 564/153

FOREIGN PATENT DOCUMENTS

| EP | 2281791 A1 | 2/2011 |
| EP | 2281811 A1 | 2/2011 |
| EP | 2281814 A1 | 2/2011 |
| EP | 2281808 A1 | 9/2011 |

* cited by examiner

ALTERNATIVE PROCESS FOR THE PURIFICATION OF AN INTERMEDIATE IN THE SYNTHESIS OF NON-IONIC X-RAY CONTRAST AGENTS

CROSS-REFERENCE TO RELATED APPLICATIONS

This application is a filing under 35 U.S.C. 371 of international application number PCT/EP2014/076873, filed Dec. 8, 2014, which claims priority to U.S. application No. 61/912,807, filed Dec. 6, 2013, and which claims priority to U.S. application No. 61/969,959, filed Mar. 25, 2014, the entire disclosures of each of which are hereby incorporated by reference.

TECHNICAL FIELD

This invention relates generally to non-ionic X-ray contrast agents. It further relates to an alternative process for the production of an intermediate used in the synthesis of non-ionic X-ray contrast agents. In particular, it relates to an alternative downstream process for the production of 5-acetamido-N,N'-bis(2,3-dihydroxypropyl)-2,4,6-triiodo-isophthalamide ("Compound A"), a key intermediate in the production of iodixanol and iohexol, which are two of the biggest commercially available non-ionic x-ray contrast media agents.

BACKGROUND OF THE INVENTION

Non-ionic X-ray contrast agents constitute a very important class of pharmaceutical compounds produced in large quantities. 5-[N-(2,3-dihydroxypropyl)-acetamido]-N,N'-bis(2,3-dihydroxypropyl)-2,4,6-triiodo-isophthalamide ("iohexol"), 5-[N-(2-hydroxy-3-methoxypropyl)acetamido]-N,N'-bis(2,3-dihydroxypropyl)-2,4,6-triiodo-isophthalamide ("iopentol") and 1,3-bis(acetamido)-N,N'-bis[3,5-bis(2,3-dihydroxypropylaminocarbonyl)-2,4,6-triiodophenyl]-2-hydroxypropane ("iodixanol") are important examples of such compounds. They generally contain one or two triiodinated benzene rings.

The industrial production of non-ionic X-ray contrast agents involves a multistep chemical synthesis. To reduce the cost of the final product, it is critical to optimize the yield in each step. Even a small increase in yield can lead to significant savings in a large scale production. In particular, iodine is one of the most expensive reagent in the process. It is thus especially important to obtain a high yield with few by-products and minimal wastage for each synthetic intermediate involving an iodinated compound. Furthermore, improved purity of a reaction intermediate, especially at the latter stage of synthesis, is essential in providing a final drug substance fulfilling regulatory specification such as those expressed on US Pharmacopeia. In addition to economic and regulatory concerns, the environmental impact of an industrial process is becoming an increasingly significant consideration in the design and optimization of synthetic procedures.

One process by which iodixanol (1,3-bis(acetamido)-N,N'-bis[3,5-bis(2,3-dihydroxypropylaminocarbonyl)-2,4,6-triiodophenyl]-2-hydroxypropane) can be prepared is according to Scheme 1 below starting from 5-nitroisophthalic acid. See also U.S. Pat. No. 6,974,882. As part of the established acetylation process, intermediate 5-amino-N,N'-bis(2,3-dihydroxypropyl)-2,4,6-triiodo-1,3-benzenedicarboxamide) ("Compound B") is acetylated to give overacetylated 5-acetamido-N,N'-bis(2,3-dihydroxypropyl)-2,4,6-triiodoisophthalamide ("Compound A"). Subsequently overacetylated Compound A is deacetylated to remove O-acetyl groups formed during the previous acetylation reaction to give Compound A. After deacetylation, Compound A can be purified (e.g., by crystallization). The purified Compound A can then be isolated. The isolated Compound A can then be dried for storage or it may be used directly in the production of iodixanol (e.g., dimerization of Compound A in the presence of epichlorohydrin results in the formation of iodixanol).

Scheme I

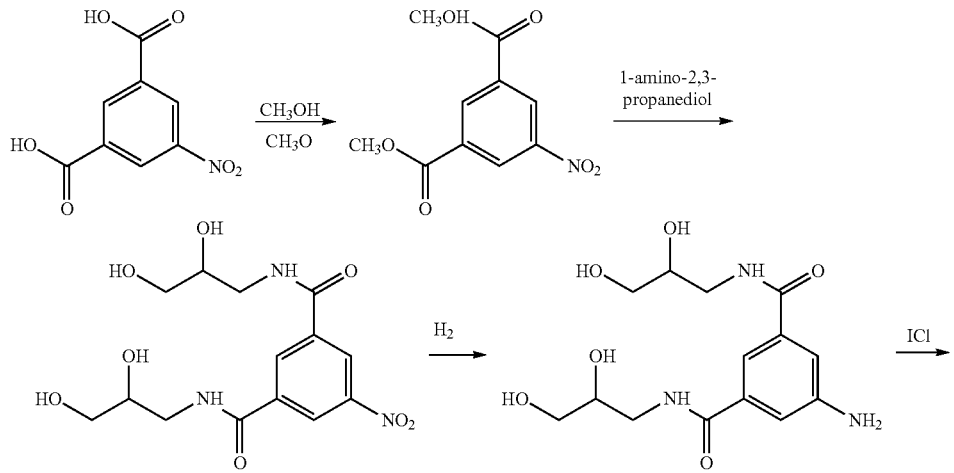

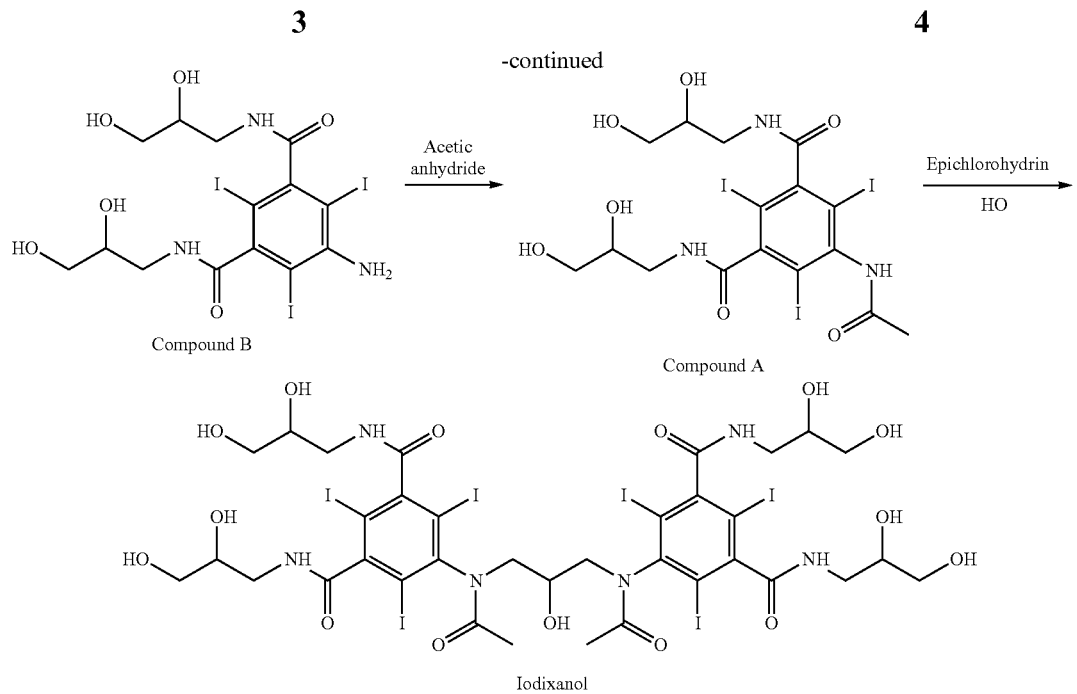

Compound B

Compound A

Iodixanol

Consequently, the conversion of Compound B to Compound A is a key and important step in the both the small-scale and industrial scale production of iodixanol.

There exists a need for effective and efficient processes for the industrial scale production of intermediates such as 5-acetamido-N,N'-bis(2,3-dihydroxypropyl)-2,4,6-triiodo-isophthalamide ("Compound A"). The present invention, as described below, answers such a need by providing alternative downstream semi-continuous processes for the production of Compound A that gives a significant increase in yield and significant reduction in energy consumption and process time.

SUMMARY OF THE INVENTION

Figure 1:
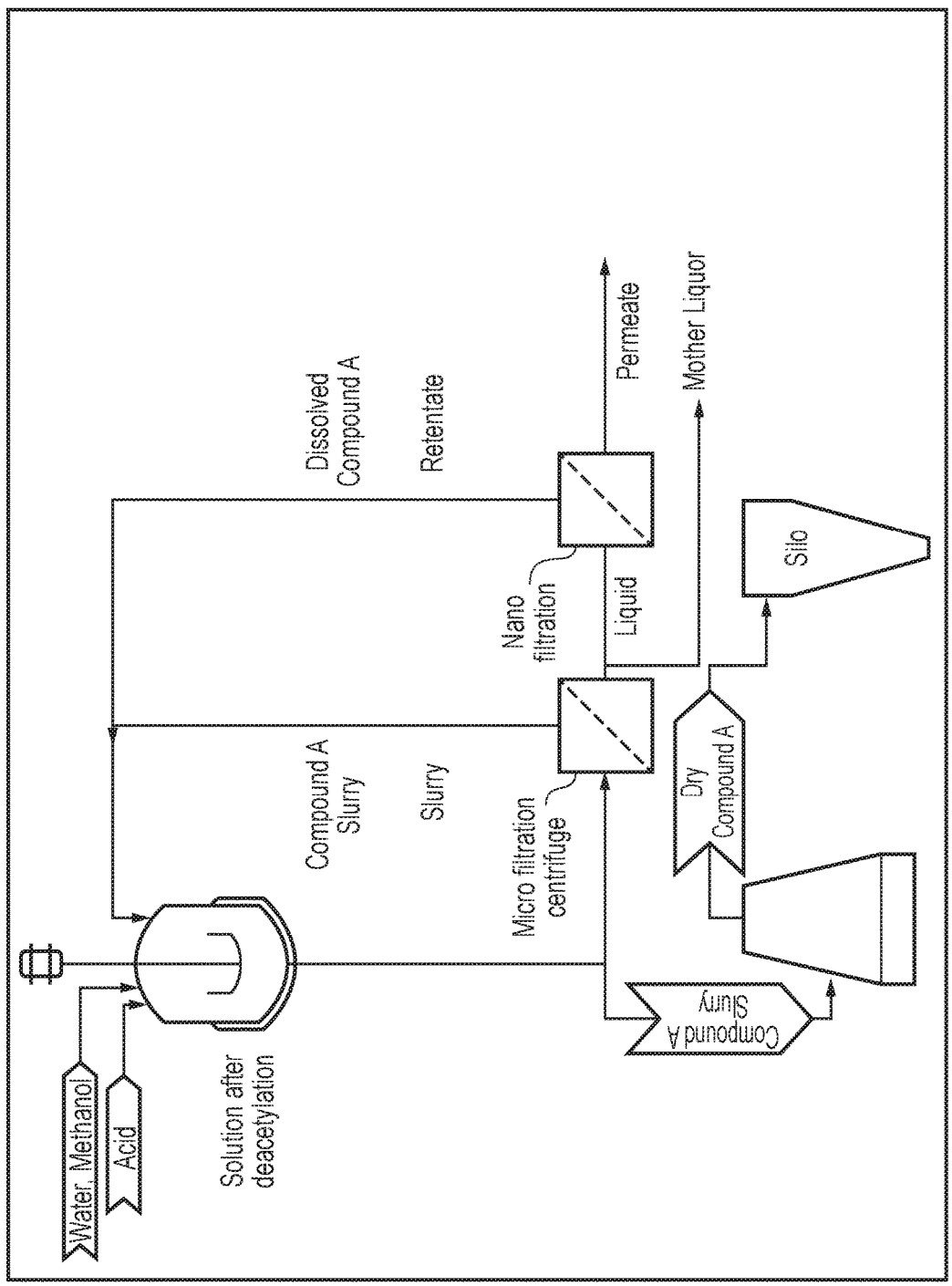
FIG. 1 illustrates downstream continuous processing of the solution comprising crude Compound A resulting from the alternative acetylation process described herein and simple crystallization of 5-acetamido-N,N'-bis(2,3-dihydroxypropyl)-2,4,6-triiodoisophthalamide ("Compound A").

The present invention provides an alternative process for the acetylation of 5-amino-N, N'-bis(2,3-dihydroxypropyl)-2,4,6-triiodo-1,3-benzenedicarboxamide) ("Compound B") to form Compound A followed by an alternative continuous downstream process for the production of 5-acetamido-N, N'-bis(2,3-dihydroxypropyl)-2,4,6-triiodoisophthalamide ("Compound A") comprising precipitation, purification (e.g., a separation system such as microfiltration or centrifuge, a membrane filtration system (e.g., nanofiltration system)), and drying.

The present invention provides an alternative process for the acetylation of 5-amino-N,N'-bis(2,3-dihydroxypropyl)-2,4,6-triiodo-1,3-benzenedicarboxamide) ("Compound B") to form Compound A followed by an alternative continuous downstream process for the production of 5-acetamido-N, N'-bis(2,3-dihydroxypropyl)-2,4,6-triiodoisophthalamide ("Compound A") comprising a membrane filtration system (e.g., nanofiltration system) without the need for crystallization and drying.

The present invention provides an alternative continuous downstream process for the production of 5-acetamido-N, N'-bis(2,3-dihydroxypropyl)-2,4,6-triiodoisophthalamide ("Compound A") comprising precipitation, purification (e.g., a separation system such as microfiltration or centrifuge, a membrane filtration system (e.g., nanofiltration system)), and drying.

The present invention provides an alternative continuous downstream process for the production of 5-acetamido-N, N'-bis(2,3-dihydroxypropyl)-2,4,6-triiodoisophthalamide ("Compound A") comprising a membrane filtration system (e.g., nanofiltration system) without the need for crystallization and drying.

The present invention provides a process comprising the steps of:

(i) reacting 5-amino-N,N'-bis(2,3-dihydroxypropyl)-2,4,6-triiodoisophthalamide ("Compound B") with a mixture of acetic anhydride/acetic acid to form a first slurry;

(ii) heating said first slurry to about 60° C.;

(iii) adding an acid catalyst (preferably, para-toluene sulfonic acid (PTSA)) to said slurry at a rate such that the reaction temperature is maintained at a temperature range of about 65-85° C.;

(iv) adding a deacetylating agent to the reaction mixture of step (iii) to form a reaction mixture comprising Compound A;

(v) purifying the reaction mixture of step (iv) comprising Compound A wherein said purifying step comprises the steps of:

(vi) passing said reaction mixture of step (iv) comprising Compound A through a separation system to create a second slurry and a liquid;

(vii) collecting the second slurry of step (vi) and repeating step (v);

(viii) collecting the liquid of step (vi) and passing it through a membrane filtration system;

(ix) collecting the retentate of step (viii) and repeating step (v); and (x) continuously repeating steps (v)-(ix).

According to the process of the invention, the process may further comprise the step of: (xii) drying the reaction mixture of step (iv) comprising Compound A.

The present invention provides a process comprising the steps of:

(i) reacting 5-amino-N,N'-bis(2,3-dihydroxypropyl)-2,4,6-triiodoisophthalamide ("Compound B") with a mixture of acetic anhydride/acetic acid to form a slurry;

(ii) heating said slurry to about 60° C.;

(iii) adding an acid catalyst (preferably, para-toluene sulfonic acid (PTSA)) to said slurry at a rate such that the reaction temperature is maintained at a temperature range of about 65-85° C.;

(iv) adding a deacetylating agent to the reaction mixture of step (iii) to form a reaction mixture comprising Compound A;

(v) purifying the reaction mixture of step (iv) comprising Compound A wherein said purifying step comprises the steps of:

(vi) passing said reaction mixture of step (iv) comprising Compound A through a membrane filtration system;

(vii) collecting the retentate of step (vi) and repeating step (v); and (viii) continuously repeating steps (v)-(vii).

According to the process of the invention, the membrane filtration system comprises a nanofiltration system as described herein.

According to the process of the invention, the process may further comprise the step of: alkylating the reaction mixture of step (iv) comprising Compound A.

According to the process of the invention, the process may further comprise the step of: bis-alkylating or dimerizing the reaction mixture of step (iv) comprising Compound A.

DETAILED DESCRIPTION OF THE INVENTION

In the established industrial scale process, Compound B is added to a mixture of acetic anhydride and acetic acid. The resulting slurry is then heated to approximately 60° C. When the temperature is achieved, an acid catalyst (e.g., para-toluene sulfonic acid (PTSA)(s)) is added in one portion in catalytic amounts. Despite maximum cooling in the reactor jacket, the temperature of the reaction mixture increases rapidly to about 120-125° C. due to the exothermic acetylation reaction. The main part of the acetylation reaction will accordingly occur at 120-125° C. Because of the high reaction temperature, considerable levels of the following by-products I, II, and III in addition to Compound A are formed:

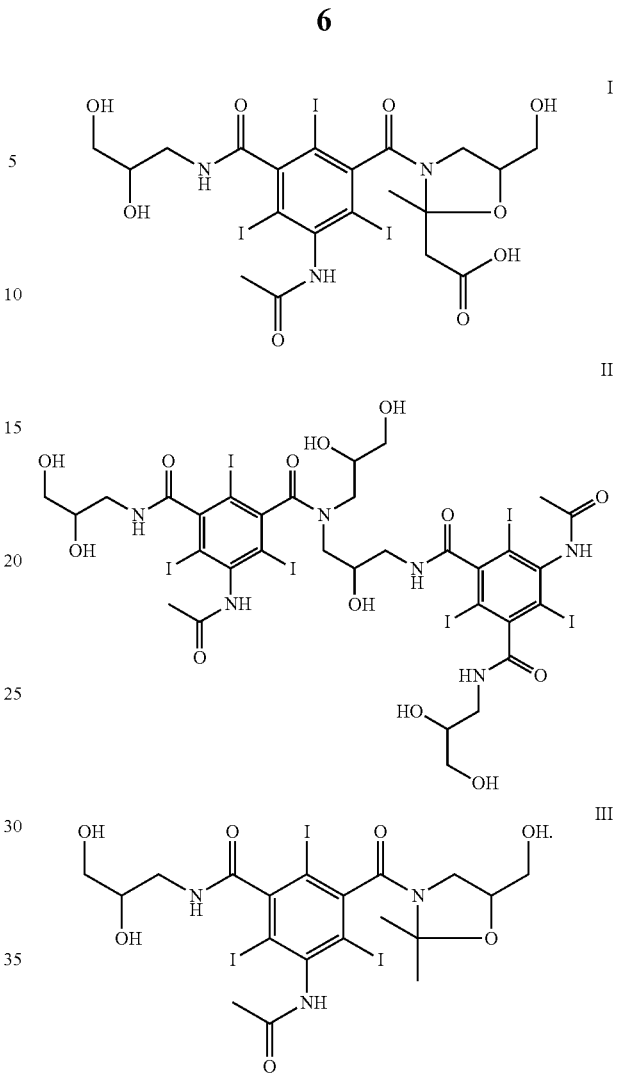

According to the present invention, an alternative acetylation process is provided. According to the present invention, Compound B is added to a mixture of acetic anhydride and acetic acid. The resulting slurry is then heated to approximately 60° C. At this temperature, a catalytic amount of an acid catalyst is added. Examples of a suitable acid catalyst include, for example, a sulfonic acid such as methanesulfonic acid, para-toluenesulfonic acid (PTSA) and sulphuric acid. Of these, para-toluenesulfonic acid (PTSA) is preferred. According to the invention, the acid catalyst can be added as a solid or as a solution. Examples of suitable solvents to form such a solution include acetic acid, acetic anhydride or a mixture of acetic acid and acetic anhydride. The addition is performed carefully while the temperature is controlled. In one embodiment, the PTSA is added as a solid in several portions. In one embodiment, the PTSA is added as a solution where PTSA is dissolved in a small volume of acetic acid. In one embodiment, the PTSA is added as a solution where PTSA is dissolved in a small volume of acetic anhydride. In one embodiment, the PTSA is added as a solution where PTSA is dissolved in a small volume of a mixture of acetic acid and acetic anhydride. The rate/speed of the addition of the acid catalyst, preferably PTSA, is such that the maximum reaction temperature is maintained at about 65-85° C.

In a preferred embodiment, the rate/speed of the addition of the acid catalyst, preferably PTSA, is such that the maximum reaction temperature is maintained at about 70-80° C.

According to the present invention, addition of the acid catalyst, preferably PTSA, over time to control temperature produces a reaction mixture comprising overacetylated Compound A with lower levels of by-products as described herein compared to the established acetylation process. The reaction mixture comprising overacetylated Compound A can then be deacetylated using a deacetylating agent. There is no particular restriction upon the nature of the deacylating agent used, and any deacylating agent commonly used in conventional reactions may equally be used here. Examples of suitable deacylating agents include aqueous inorganic bases including alkali metal carbonates, such as sodium carbonate, potassium carbonate or lithium carbonate; and alkali metal hydroxides, such as sodium hydroxide, potassium hydroxide or lithium hydroxide. Of these, the alkali metal hydroxides, particularly sodium hydroxide or potassium hydroxide, and most preferably sodium hydroxide are preferred. For example, the reaction mixture comprising overacetylated Compound A can be deacetylated by the addition of base, such as sodium hydroxide, to form Compound A which in turn can then be purified (e.g., crystallization) and isolated by techniques known in the art.

According to the invention, as a result of the alternative acetylation process described herein, the by-product profile is improved, which makes it possible to simplify the post deacetylation purification of the 5-acetamido-N,N'-bis(2,3-dihydroxypropyl)-2,4,6-triiodoisophthalamide ("Compound A") and to isolate purified Compound A in higher yields.

As described above, by-products are formed during the acetylation of 5-amino-N, N'-bis(2,3-dihydroxypropyl)-2,4,6-triiodo-1,3-benzenedicarboxamide) ("Compound B"). In the established acetylation process, the by-products that form are at such a level that a crystallization step is necessary to remove them from 5-acetamido-N,N'-bis(2,3-dihydroxypropyl)-2,4,6-triiodoisophthalamide ("Compound A") prior to using Compound A in the synthesis of x-ray contrast media agents such as iodixanol and iohexol. If no crystallization step is performed, then additional purification steps need to be included later in the process which results in more production costs which is not ideal for industrial scale production.

It has now been found that the purity of 5-acetamido-N,N'-bis(2,3-dihydroxypropyl)-2,4,6-triiodoisophthalamide ("Compound A") before crystallization measured as HPLC [area %] with the original acetylation is 97.7% and with the alternative acetylation process described herein 99.2%. The alternative acetylation process reduces the formation of by-products.

In the alternative acetylation process, the process temperature is decreased from about 115-125° C. to about 65-85° C. and the ratio between acetic anhydride and acetic acid in the process solution is reduced significantly as well. Table 1 summarizes the change in by-product profile and the corresponding HPLC [area %] between the original and alternative acetylation process.

TABLE 1

By-products prior to crystallization with original and alternative acetylation

| Compound | Original acetylation process [HPLC area %] | Alternative acetylation process [HPLC area %] |
| --- | --- | --- |
| Compound A Purity | 97.7 | 99.2 |
| Compound B remaining post acetylation | 0.13 | 0.03 |
| By-products I and II | 1.25 | 0.25 |
| By-product III | 0.33 | 0.01 |

In the established acetylation process, salt by-products (e.g. sodium chloride and sodium acetate) are removed from 5-acetamido-N,N'-bis(2,3-dihydroxypropyl)-2,4,6-triiodo-isophthalamide ("Compound A") during a crystallization and filtration step. pH and temperature in solution is under strict control. Seeding to control crystallization is executed at a certain pH and temperature. The pH is adjusted to about 2.0-8.0, preferably about 5.0-8.0 and most preferably about 7. The temperature is maintained at about 10-25° C., preferably about 20° C. Then the crystallization process is allowed to run for approx. 24 hours before the slurry is carefully transferred to a pressure filter. On the pressure filter, the mother liquor is removed. Then the filter cake is carefully agitated before washing liquid is applied. The filter cake is partly dried on the filter by blowing a huge amount of hot gas through the cake. Total residence time on the pressure filter is approx. 24 hours. Partly dried filter cake is then transferred to an indirect batch dryer. Dry 5-acetamido-N,N'-bis(2,3-dihydroxypropyl)-2,4,6-triiodoisophthalamide ("Compound A") is then milled to destroy lumps generated during drying.

The present invention now provides two alternative continuous purification processes that eliminate the need for the established crystallization step. Each of the purification processes of the present invention can be used with either the established or alternative acetylation process. In a preferred embodiment, each of the purification processes is used subsequent to the alternative acetylation process described herein.

It has now been found that purification of Compound A can be achieved by using membrane filtration where low molecular weight by-products and salts are collected in the permeate and 5-acetamido-N,N'-bis(2,3-dihydroxypropyl)-2,4,6-triiodoisophthalamide ("Compound A") is collected in the retentate.

According to a process of the invention, the separation system can be any separation system capable of providing a liquid as particle free as possible prior to passing the liquid through the membrane filtration system, as described herein. In one embodiment of the invention, the separation system comprises a microfiltration system (e.g., crossflow microfiltration). In one embodiment of the invention, the separation system comprises a centrifuge. According to the invention, any microfiltration system known in the art may be used. According to the invention, any centrifuge capable of separating particles from the liquid may be used (e.g., a decanter centrifuge).

According to the invention, a suitable "membrane filtration system" includes any membrane filtration technique known in the art. In one embodiment of the invention, the membrane filtration system comprises a nanofiltration system. Any nanofiltration system known in the art may be used.

The alternative continuous downstream processes of the invention allows for an increase in the overall yield of 5-acetamido-N,N'-bis(2,3-dihydroxypropyl)-2,4,6-triiodo-isophthalamide ("Compound A"), reduce process time and labour costs. The alternative continuous downstream processes of the invention further offer the advantage of providing a stabilized process by removing a complex and manual crystallization and isolation step used in the established acetylation process to form Compound A as described above.

Alternative Process 1:

Alternative process 1, exemplified in FIG. 1, includes a simple precipitation step to reduce pH and viscosity in the solution comprising desired Compound A. Particle size and distribution of 5-acetamido-N,N'-bis(2,3-dihydroxypropyl)-2,4,6-triiodoisophthalamide ("Compound A") is not critical as it is in the established acetylation process because no filter cake is going to be handled.

After precipitation, the slurry can, if needed, be filtered using an appropriate particle-liquid separation technique known in the art (e.g. crossflow microfiltration or decanter centrifuge) to separate the reaction mixture into 5-acetamido-N,N'-bis(2,3-dihydroxypropyl)-2,4,6-triiodo-isophthalamide ("Compound A") solids (i.e. slurry) and liquid. The removed solids (i.e., slurry) are circulated back to the reactor. Removal of slurry is performed to protect the membrane filtration system (e.g., nanofiltration membrane) through which the liquid is passed and increase its capacity.

The liquid from the separation system contains dissolved 5-acetamido-N,N'-bis(2,3-dihydroxypropyl)-2,4,6-triiodo-isophthalamide ("Compound A"), salts and by-products. The liquid is then passed through a membrane filtration system (e.g., nanofiltration membrane of the cross flow type) that is resistant to methanol at neutral to acidic pH and has a cut-off that allows the passing of low molecular weight by-products (<app. 300 dalton) or small molecules as salts to be collected in permeate together with only small amounts of 5-acetamido-N,N'-bis(2,3-dihydroxypropyl)-2,4,6-tri-iodoisophthalamide ("Compound A"). The membrane filtration system (e.g., nanofiltration membrane) reduces 5-acetamido-N,N'-bis(2,3-dihydroxypropyl)-2,4,6-triiodoisophthalamide ("Compound A") yield loss to a minimum as it is separated into the retentate while effectively removing by-products in the permeate. The retentate produced by the membrane filtration system contains the majority of the 5-acetamido-N,N'-bis(2,3-dihydroxypropyl)-2,4,6-triiodoisophthalamide ("Compound A") and is fed back into the reactor.

Any remaining salts and other low molecular weight by-products in the retentate can be removed with methanol, water, or a mixture thereof. Methanol, water, or a mixture thereof is added to reactor during circulation of the solution via the separation system and the membrane filtration system, each as described herein. Volume and pH in the reactor is monitored to keep suitable conditions for optimized membrane filtration.

To further reduce the amount of by-products, parts of the liquid where by-products are concentrated, can optionally be removed as mother liquor from the system, see FIG. 1.

When the levels of salts and by-products have been achieved, the product slurry may be concentrated even more by stopping the methanol addition into the reactor while the circulation of the solution via the separation system and the membrane filtration system is still going. This alternative downstream process is performed continuously until the level of salts is not more than (NMT) 1.5 wt % and the level of by-products is NMT 2.0 area % in the dry Compound A obtained.

Once Compound A has achieved a such a purity profile, it can be dried using a continuous, direct dryer to give a lump free powder of 5-acetamido-N,N'-bis(2,3-dihydroxypropyl)-2,4,6-triiodoisophthalamide ("Compound A") which can then be subsequently stored. According to the invention, this alternative process 1 can be automated.

Figure 2:
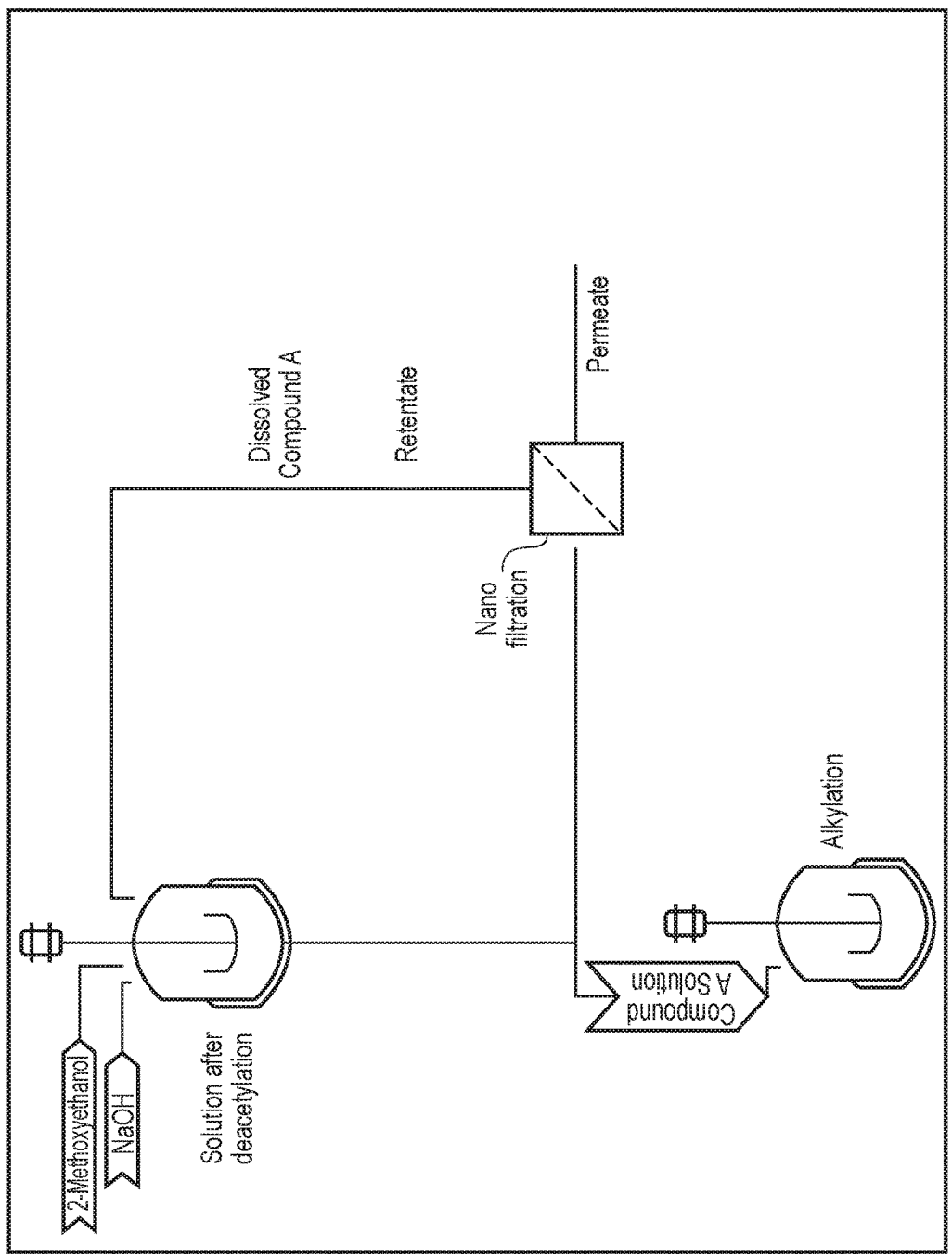
FIG. 2 illustrates downstream continuous processing of the solution after deacetylation with alternative acetylation and no crystallization and drying of 5-acetamido-N,N'-bis(2,3-dihydroxypropyl)-2,4,6-triiodoisophthalamide ("Compound A").

Alternative Process 2:

In Alternative process 2, as illustrated in FIG. 2, the crude reaction solution after deacetylation is fed into a reactor and kept at pH>11 to keep 5-acetamido-N,N'-bis(2,3-dihydroxypropyl)-2,4,6-triiodoisophthalamide ("Compound A") dissolved. In order to prepare the solution for directly use in the syntheses of iohexol and iodixanol, the water in the solution has to be replaced by solvents such as methanol, which in turn can optionally be replaced by 2-methoxyethanol in a nanofiltration system with a membrane with appropriate cut-off that withstands solvents and high pH. The salts and low molecular weight by-products are collected in the permeate. 5-acetamido-N,N'-bis(2,3-dihydroxypropyl)-2,4,6-triiodoisophthalamide ("Compound A") is collected in the retentate. The use of a nanofiltration system allows for concentration adjustment of 5-acetamido-N,N'-bis(2,3-dihydroxypropyl)-2,4,6-triiodoisophthalamide ("Compound A") before being fed back into the reactor. By adjusting the concentration and process time, production capacity and investments cost/operational costs can be optimized. Alternative process 2 is continuous until the level of salts is NMT 1.5 wt % and the level of by-products is NMT 2.0 area % in the Compound A solution.

Once such a purity profile of Compound A is achieved, then the Compound A can be directly used to synthesize x-ray contrast media agents such as iohexol and iodixanol via alkylation and bis-alkylation (dimerization) respectively. Alternative process 2 eliminates the need for a drying step as used in the established process and in alternative process 1. Since the drying step can be eliminated, Alternative process 2 also offers the advantage of the need for storage of Compound A. According to the invention, this alternative process 2 can be automated.

As illustrated in Table 2, Alternative process 1 and Alternative process 2, provide comparable quality and yields as compared to the established original process. In addition, the processes offer the advantage of improved energy savings and reduction in overall production time.

TABLE 2

Changes in key parameters in the modified processes

| | Original process | Alternative process 1 | Alternative process 2 |
|---|---|---|---|
| Compound A Purity | 99.5% | 99.2-99.5% | Ca. 99.2% |
| Yield | 96.2% | 97-99% | 99.2% |
| Energy savings* | — | Much | Very much |
| Reduction of process time* | — | Ca. 25% | >60% |

*as compared to the already established process.

What is claimed:

1. A process comprising the steps of:
   (i) reacting 5-amino-N,N'-bis(2,3-dihydroxypropyl)-2,4,6-triiodoisophthalamide ("Compound B") with a mixture of acetic anhydride/acetic acid to form a slurry;
   (ii) heating said slurry to about 60° C.;

(iii) adding an acid catalyst to said slurry at a rate such that the reaction temperature is maintained at a temperature range of about 65-85° C.;

(iv) adding a deacetylating agent to the reaction mixture of step (iii) to form a reaction mixture comprising Compound A;

(v) purifying the reaction mixture of step (iv) comprising Compound A wherein said purifying step comprises the steps of:

(vi) passing said reaction mixture of step (iv) comprising Compound A through a membrane filtration system;

(vii) collecting the retentate of step (vi) and repeating step (v); and (viii) continuously repeating steps (v)-(vii), to obtain a purified Compound A.

2. The process according to claim 1, wherein said membrane filtration system comprises a nanofiltration system.

3. The process according to claim 1, wherein step (viii) is repeated until a level of salts is not more than (NMT) 1.5 wt % and a level of by-products is NMT 2.0 area % as measured by HPLC in the purified Compound A.

4. The process according to claim 1, further comprising the step of: alkylating the purified Compound A.

5. The process according to claim 1, further comprising the step of: bis-alkylating or dimerizing the purified Compound A.

6. The process according to claim 1, wherein said acid catalyst is a sulfonic acid.

7. The process according to claim 6, wherein said acid catalyst is para-toluene sulfonic acid (PTSA).

8. The process according to claim 7, wherein said PTSA is added in a catalytic amount as a solid.

9. The process according to claim 7, wherein said PTSA is added in a catalytic amount as a solution of PTSA dissolved in a small volume of acetic anhydride.

* * * * *